United States Patent [19]

Tang

[11] Patent Number: 5,276,158

[45] Date of Patent: Jan. 4, 1994

[54] METHOD OF PREPARING 5-AMINO-3-SUBSTITUTED-PYRAZOLE

[75] Inventor: Ping-Wah Tang, Rochester, N.Y.

[73] Assignee: Eastman Kodak Company, Rochester, N.Y.

[21] Appl. No.: 841,469

[22] Filed: Feb. 26, 1992

[51] Int. Cl.$^5$ ............................................. C07D 231/38
[52] U.S. Cl. ................................ 548/371.4; 548/247; 548/365.7; 548/306.1
[58] Field of Search ............. 548/374, 375, 247, 371.4

[56] References Cited

U.S. PATENT DOCUMENTS 4,540,654  9/1985  Sato et al. ............................ 548/374
4,924,002  5/1990  Kostlan ................................ 548/374

OTHER PUBLICATIONS

Wiley, *Pyrazoles, Pyrazolines, Pyrazolidines, Indazoles and Condensed Rings,* (1967), p. 56.
Lin et al, Journal of Heterocyclic Chemistry, vol. 14 (1977) pp. 345–347.
Katritzky, Comprehensive Heterocyclic Chemistry, vol. 6 (1986) pp. 62–63.

*Primary Examiner*—Robert W. Ramsuer
*Attorney, Agent, or Firm*—Arthur E. Kluegel

[57] ABSTRACT

A process of preparing a 5-amino-3-substituted pyrazole of formula (I)

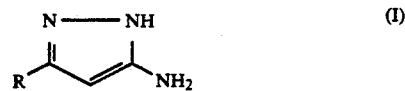

wherein R is an optionally substituted alkyl group or an optionally substituted aryl group, said process comprising reacting a compound of formula (III)

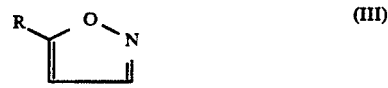

with $H_2NNH_2$ to obtain the compound of formula (I). The compound of formula (III) can be obtained by reacting a ketone of the formula $R\text{-}CO\text{-}CH_3$ with DMF—acetal ($HC(OCH_3)_2N(CH_3)_2$) followed by subsequent reaction with $NH_2OH \cdot HCl$.

10 Claims, No Drawings

METHOD OF PREPARING 5-AMINO-3-SUBSTITUTED-PYRAZOLE

BACKGROUND OF THE INVENTION

The present invention relates to a method of preparing pyrazole compounds of the following formula (I):

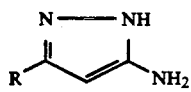

wherein R is an optionally substituted alkyl group, and optionally substituted aryl group or an optionally substituted heterocyclic group.

The compounds of formula (I) are useful as intermediates in the preparation of pyrazolotriazole dye-forming couplers employed in photographic silver halide materials. For example, a typical coupler can be represented by the general formula (II):

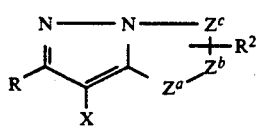

wherein $R^2$ is a substituent know in the photographic art; X is hydrogen or a coupling-off group known in the photographic art; and $Z^a$, $Z^b$ and $Z^c$ are independently a substituted or unsubstituted methine group, =N-, =C- or -NH-, provided that one of either the $Z^a$—$Z^b$ bond or the $Z^b$—$Z^c$ bond is a double bond and the other is a single bond, and when the $Z^b$—$Z^c$ bond is a carbon—carbon double bond, it may form part of an aromatic ring, and at least one of $Z^a$, $Z^B$ and $Z^c$ represents a methine group connect with the group $R^2$.

One class of pyrazolotriazole couplers includes 1H-pyrazolo[1,5b][1,2,4]triazole couplers, such as described in European Patent 1777765. These couplers can be represented by the general formula:

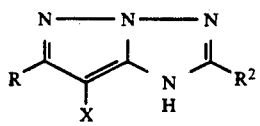

wherein R and $R^2$ are as defined above.

Another class of pyrazolotriazole couplers include 1H-pyrazol [3,2-]-5-triazole couplers, such as described in U.S. Pat. Nos. 3,725,067 and 4,812,576. These couplers can be represented by the general formula:

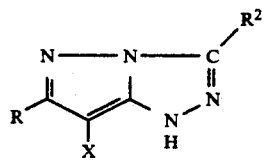

wherein R and $R^2$ are as defined above.

The intermediate compounds of formula (I) can be used to form pyrazolotriazole couplers according to methods known in the art. Such methods are disclosed in U.S. Pat. Nos. 4,540,654 and 4,812,576.

The method according to the presently claimed method has the advantage that the starting materials are commercially available. Additionally, the reagents pose no significant health or disposal risks. The method avoids the use of reagents which, if present as residual materials, would be undesirable in further processing of photographic elements.

SUMMARY OF THE INVENTION

In a first aspect, the method according to the present invention relates to the production of compounds of formula (I) from compounds of formula (III) according to the following reaction Scheme A:

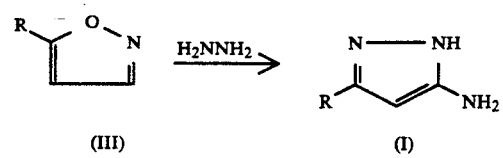

In a second aspect, the method includes the production of compounds of formula (I) wherein the compounds of formula (III) are produced according to the following reaction Scheme B.

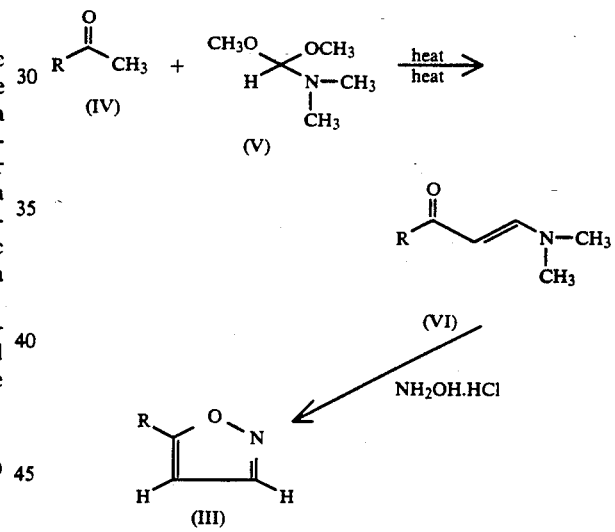

R in the above formulae corresponds to R in formulae (I) and (II).

DESCRIPTION OF THE PREFERRED EMBODIMENTS

In the above formulae, R represents an optionally substituted alkyl group, an optionally substituted aryl group or an optionally substituted heterocyclic group. When R is an alkyl group, the alkyl group may be straight, branched or cyclic. Examples of an optionally substituted alkyl group include t-butyl, trifluoromethyl, tridecyl or 3-(2,4-di-t-amylphenoxy) propyl. Examples of an optionally substituted heterocyclic group included a 3 to 7 members heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl.

Substituents for the substituted alkyl, aryl or heterocyclic groups include those known in the photographic art which do not prohibit the reaction mechanism. Suitable substituents include: halogen; an aryloxy group; a heterocyclic oxy group or heterocyclic thio group, each of which may be substituted and which contain a 3 to 7 membered heterocyclic ring composed of carbon atoms and at least one hetero atom selected from the group consisting of oxygen, nitrogen and sulfur; cyano; an alkoxy group; an acyloxy group; a carbamoyloxy group; a silyloxy group; a sulfonyloxy group; an acylamino group; an anilino group; a uredido group; an imido group; a sulfonylamino group; a carbamoylamino group; an alkylthio group; an arylthio group; an alkoxycarbonylamino group; an aryloxycarbonylamino group; a sulfonamido group; a carbamoyl group; an acyl group; a sulfamoyl group; a sulfonyl group; a sulfinyl group; a alkoxycarbonyl group; an aryloxycarbonyl group; an alkenyl group; a carboxyl group; a sulfo group; hydroxyl; an amino group; or a carbonamido group.

Additionally, the substituents for R as a substituted alkyl or heterocyclic group further include an optionally substituted aryl group, wherein the optionally substituted aryl group is defined the same as above. The substituents for R as a substituted aryl or heterocyclic group further include an optionally substituted alkyl group, wherein the optionally substituted alkyl group is defined the same as above.

Generally, the alkyl group of R, or the substituents thereof which contain an alkyl moiety, contain 1 to 16 carbon atoms. The aryl group of R, or the substituents thereof which contain an aryl group, contain 6 to 8 carbon atoms.

Preferably, the substituent R group is directly attached to the carbonyl group in formula (IV), and accordingly to the pyrazole ring in formula (I) or the isoxazole ring in formula (III), through a carbon atom which is not bonded to a hydrogen atom. Such groups include tert-butyl, tert-pentyl, tert-octyl, adamantryl, 1-methylcyclohexyl, substituted phenyl or a substituted heterocyclic group. Such R groups prevent the formation of undesired side products in the reaction of ketone (VI) with compound (V) in the preparation of isoxazole compounds of formula (III).

In Scheme A, the production of compound (I) from compound (III) is conducted in the presence of $H_2NNH_2$ to provide for formation of the pyrazole ring. Preferably, this reaction is conducted in the absence of other bases. Preferably, the solvent used in this reaction is an alcohol, and preferred alcohols are methanol, ethanol, propanol, isopropanol, etc. The preferred temperature is 65° C. to 110° C., and the preferred reaction time is 4 to 24 hours.

In Scheme B, compounds (IV) and (V) are available products, and accordingly, compounds of formula (I) can be obtained from available materials. The reaction of compounds (IV) and (V) is preferably conducted in the absence of a solvent. This reaction forms a precursor of formula (VI)

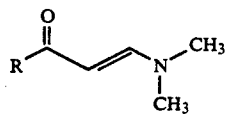 (VI)

which is subjected to cyclization through reaction of an agent such as $NH_2OH \cdot HCl$ to form the compound of formula (III).

The preparation of the enaminone intermediate of formula (VI) from the methyl ketone of formula (IV) is preferably conducted in the presence of excess of dimethylformamide dimethyl acetal (V) without the use of a solvent. The preferred temperatures are in the range of 80° to 130° C. and the preferred reaction time is 4 to 40 hours. The cyclization step leading to the isoxazole of formula (III) from the enaminone of formula (VI) is preferably conducted in a water-soluble solvent, such as dioxane, tetrahydrofuran, 1,2-dimethoxyethane, etc. This step is carried out in the presence of water. The preferred reaction temperature is 0° to 50° C., and the preferred reaction time is 5 to 24 hours.

Illustrative 5-amino-3-substituted pyrazoles of formula (I) which can be prepared according to the present invention are as follows, and each of the following compounds are useful as key starting materials for producing dye-forming couplers of formula (II).

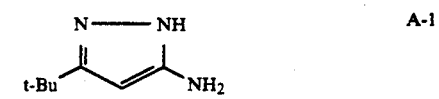 A-1

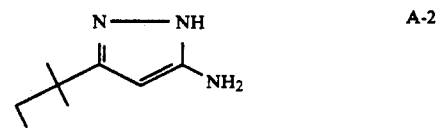 A-2

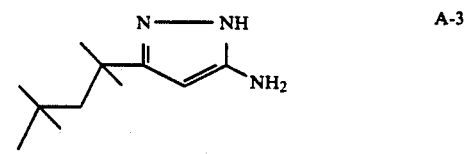 A-3

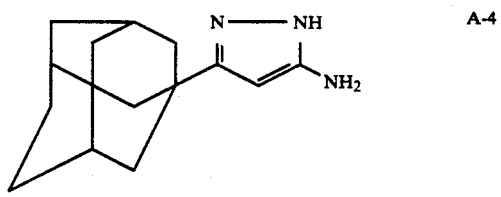 A-4

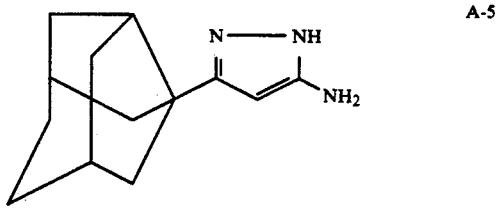 A-5

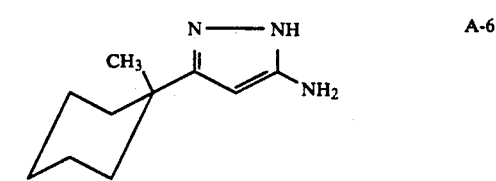 A-6

The following examples further illustrate preferred embodiments of the present invention.

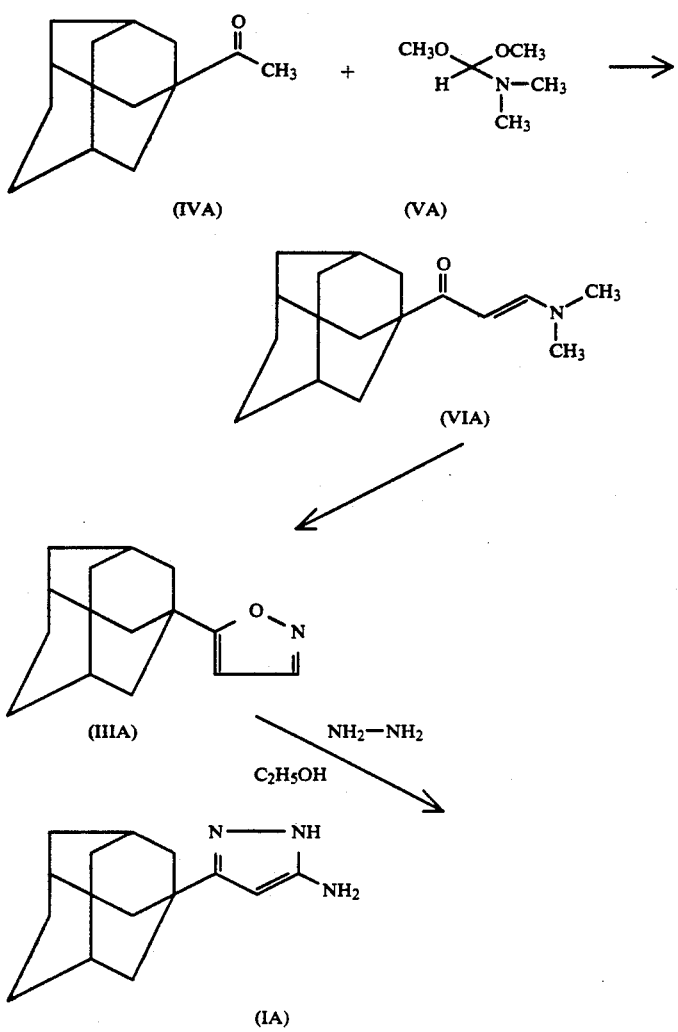

Preparation of 1-adamantyl-3-dimethylamino-2-propen-1-one—Compound (VIA)

A solution of 17.83 g (0.10 mol) of 1-adamantyl methyl ketone in 35.75 g (0.30 mol) of dimethylformamide dimethylacetal was heated at reflux for 24 hours. After cooling and removal of the solvent in vacuo at 45° to 50° C., the residue was purified by silical gel chromatography to yield 8.64 g (37%) of a white solid: $R_f$ 0.20 in 50% EtOAc/Ligroin; $^1$H NMR (CDCl$_3$) δ 1.68 (S, 6H, the δ hydrogens of the adamantyl ring, methylene protons at the farthest position from the substituent), 1.81 (S, 6H, the β hydrogens of the adamantyl ring, methylene protons at the closest position to the substituent), 2.00 (S, 3H, the three bridgehead protons, 2.90 (br S, 6H, N(CH$_3$)$_2$), 5.20 (d, 1H, J=14 Hz, O=C-CH), 7.60 (d 1H, J=14 Hz, =C-N<). All analytical data confirmed the assigned structure.

Preparation of 5-adamantylisoxazole—Compound (IIIA)

A suspension of 3.04 g (0.013 mol) of 1-adamantyle-3-dimethylamino-2-propen-1-one (VIA) and 1.0 g (0.0143 mol) of hydroxylamine hydrochloride in 25 ml of para-dioxane was stirred at room temperature for several minutes, followed by the addition of 5 ml of water. The mixture was stirred at room temperature for 24 hours and then diluted with 200 ml of ethyl acetate and 40 ml of water. The mixture was basified to pH 8, followed by partition of layers. The aqueous layer was extracted with two 60-ml portions of ethyl acetate. The combined organic extracts were washed with one 50-ml portion of water and dried over anhydrous Na$_2$SO$_4$. After filtration, the filtrate was concentrated in vacuo to yield 2.41 g (91%) of a light brown oil: $^1$H NMR (CDCl$_3$) δ 1.77 (S, 6H, the δ hydrogens of the adamantyl ring), 1.97 (S, 6H, the β hydrogens of the adamantyl ring), 2.06 (S, 3H, the three bridge head protons), 5.87 (S, 1H, —C=CH—), 8.11 (S, 1H, —N=CH—). All analytical data confirmed the assigned structure. The isoxazole was immediately used in the next step.

Preparation of 3-adamantyl-5-aminopyrazole—Compound (IA)

A solution of 2.40 g (11.80 mmol) of 5-adamantylisoxazole and 1.18 g (23.60 mmol) of hydrazine hours. The solvent was removed in vacuo and the residue was taken up in 50 mol of dichloromethane. The solution was concentrated in vacuo to yield 2.47 g (96%) of a light brown oil. The crude material was purified by chromatography on silica gel to yield 200 g (78%) of a pale yellow solid: $R_f$ 0.45 in 2/2/1 ligroin/CH$_2$Cl$_2$/C-

H3OH; ¹H NMR (CDCl3) δ 1.51 (S, 6H, the δ hydrogens of the adamantyl ring), 1.65 (S, 6H, the β hydrogens of the adamantyl ring, 1.81 (S, 3H, the three bridgehead protons), 5.16 (S, 1H, —C═CH—). All the analytical data are identical to those obtained from an authenticated sample.

The invention has been described in detail with particular reference to preferred embodiments thereof, but it will be understood that variations and modifications can be effected within the spirit and scope of the invention.

I claim:

1. A process of preparing a 5-amino-3-substituted pyrazole of formula (I)

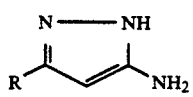
(I)

wherein R is an optionally substituted alkyl group, an optionally substituted aryl group or an optionally substituted heterocyclic group, said process comprising reacting a ketone of the formula R—CO—CH3 with HC(OCH3)2N(CH3)2 followed by reaction with NH2OH¹⁰⁸ HCl to form a compound of formula (III), and reacting the compound of formula (III)

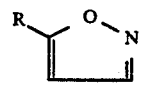
(III)

with H2NNH2 to obtain the compound of formula (I).

2. The process of claim 1, wherein R is selected from the group consisting of Tert-butyl, tert-pentyl, tert-octyl, adamantyl and 1-methylcyclohexyl.

3. The process of claim 1, wherein R is a tertiary alkyl group.

4. The process of claim 1, wherein R is adamantyl.

5. The process of claim 1, wherein R is unsubstituted or substituted phenyl.

6. The process of claim 1, wherein R is selected from the group consisting of tert-butyl, tert-pentyl, tert-octyl, adamantyl and 1-methylcyclohexyl.

7. The process of claim 1, wherein R is a tertiary alkyl group.

8. The process of claim 1, wherein R is adamantyl.

9. The process of claim 1, wherein R is unsubstituted or substituted phenyl.

10. The process of claim 1, wherein the reaction of the ketone R—CO—CH3 with HC(OCH3)2N(CH3)2 is conducted in the absence of a solvent.

* * * * *

UNITED STATES PATENT AND TRADEMARK OFFICE
CERTIFICATE OF CORRECTION

PATENT NO. : 5,276,158
DATED : January 4, 1994
INVENTOR(S) : P. Tang

It is certified that error appears in the above-identified patent and that said Letters Patent is hereby corrected as shown below:

In Column 8, line 1, delete "$NH_2OH^{108}HCl$" and insert --$NH_2OH \cdot HCl$--.

In Column 8, line 11, delete "Tert" and insert --tert--.

Signed and Sealed this

Seventeenth Day of May, 1994

Attest:

BRUCE LEHMAN

Attesting Officer    Commissioner of Patents and Trademarks